US012603170B2

(12) United States Patent (10) Patent No.: US 12,603,170 B2
Grübel et al. (45) Date of Patent: Apr. 14, 2026

(54) MEDICAL DEVICE, SYSTEM AND METHOD FOR INTERACTION WITH A SUPPLY FACILITY

(71) Applicant: Siemens Healthcare GmbH, Erlangen (DE)

(72) Inventors: Sören Grübel, Erlangen (DE); Thorsten Speckner, Erlangen (DE); Ulrich Nerreter, Nuremberg (DE)

(73) Assignee: Siemens Healthineers AG, Forchheim (DE)

( * ) Notice: Subject to any disclaimer, the term of this patent is extended or adjusted under 35 U.S.C. 154(b) by 107 days.

(21) Appl. No.: 18/513,556

(22) Filed: Nov. 18, 2023

(65) Prior Publication Data

US 2024/0170137 A1 May 23, 2024

(30) Foreign Application Priority Data

Nov. 18, 2022 (DE) ...................... 10 2022 212 368.9

(51) Int. Cl.
*G16H 40/20* (2018.01)
*G16H 40/63* (2018.01)
(52) U.S. Cl.
CPC ............. *G16H 40/20* (2018.01); *G16H 40/63* (2018.01)
(58) Field of Classification Search
CPC ......... G16H 40/20; G16H 40/63; G16H 20/40
See application file for complete search history.

(56) References Cited

U.S. PATENT DOCUMENTS

| | | | |
|---|---|---|---|
| 6,397,098 B1 * | 5/2002 | Uber, III | ................ G16H 20/17 |
| | | | 600/431 |
| 10,010,305 B2 | 7/2018 | Tsuyuki | |
| 10,290,371 B1 * | 5/2019 | Pekarske | ................ G16H 40/40 |
| 2009/0177050 A1 * | 7/2009 | Griffiths | ................ A61B 6/481 |
| | | | 600/407 |
| 2012/0196753 A1 * | 8/2012 | Laskaris | ................ F25D 19/00 |
| | | | 505/163 |
| 2014/0006052 A1 * | 1/2014 | Steinhauer | ............. G16H 20/40 |
| | | | 705/28 |
| 2015/0346296 A1 * | 12/2015 | Biber | ................ G01R 33/3804 |
| | | | 62/51.1 |

(Continued)

FOREIGN PATENT DOCUMENTS

WO 2018114403 A1 6/2018

OTHER PUBLICATIONS

I. Ahmad et al., "Emerging Technologies for Next Generation Remote Health Care and Assisted Living," in IEEE Access, vol. 10, pp. 56094-56132, 2022, doi: 10.1109/ACCESS.2022.3177278. (Year: 2022).*

(Continued)

*Primary Examiner* — Sun M Li
(74) *Attorney, Agent, or Firm* — Lempia Summerfield Katz LLC

(57) ABSTRACT

A medical device, a system including a medical device and a supply facility, and a method for operating the system are provided. For a planned activity, the medical device at least temporarily needs a resource from the supply facility. The medical device has a device control system and an interface for communication with the supply facility regarding the resource. In a notification, the medical device notifies the supply facility of a requirement for a resource.

14 Claims, 2 Drawing Sheets

(56)          References Cited

U.S. PATENT DOCUMENTS

| | | | | |
|---|---|---|---|---|
| 2016/0354562 | A1* | 12/2016 | Morrison | G08B 5/36 |
| 2017/0177807 | A1* | 6/2017 | Fabian | G16H 40/20 |
| 2019/0035501 | A1* | 1/2019 | Zhang | G16H 80/00 |
| 2019/0357309 | A1 | 11/2019 | Breunig et al. | |
| 2020/0150161 | A1 | 5/2020 | Feiweier et al. | |
| 2020/0289022 | A1* | 9/2020 | Coumans | A61G 11/00 |
| 2020/0320454 | A1* | 10/2020 | Almashor | G06Q 10/04 |
| 2021/0196576 | A1* | 7/2021 | Vinograd | G16H 40/20 |
| 2022/0331047 | A1* | 10/2022 | Shelton, IV | H04W 12/06 |
| 2022/0365499 | A1* | 11/2022 | Brown | G16H 50/20 |
| 2023/0059343 | A1* | 2/2023 | Roh | A61B 34/30 |
| 2023/0298743 | A1* | 9/2023 | Roh | A61B 90/96 |
| 2023/0377709 | A1* | 11/2023 | Shelton, IV | G16H 40/20 |

OTHER PUBLICATIONS

S. Ahmed and M. Y. A. Raja, "Telemedic sensor networks and informatics for healthcare services," 2009 6th International Symposium on High Capacity Optical Networks and Enabling Technologies (HONET), Alexandria, Egypt, 2009, pp. 67-73, doi: 10.1109/HONET.2009.5423096. (Year: 2009).*

A. Aborujilah, A.-E. F. M. Elsebaie and S. A. Mokhtar, "IoT MEMS: IoT-Based Paradigm for Medical Equipment Management Systems of ICUs in Light of COVID-19 Outbreak," in IEEE Access, vol. 9, pp. 131120-131133, 2021, doi: 10.1109/ACCESS.2021.3069255. (Year: 2021).*

Ahmad et al., "Emerging Technologies for Next Generation Remote Health Care and Assisted Living," in IEEE Access, vol. 10, pp. 56094-56132, 2022, doi: 10.1109/ACCESS.2022.3177278. (Year: 2022).*

Dar M, Swamy L, Gavin D, Theodore A. Mechanical-Ventilation Supply and Options for the COVID-19 Pandemic. Leveraging All Available Resources for a Limited Resource in a Crisis. Ann Am Thorac Soc. Mar. 2021;18(3):408-416. doi: 10.1513/AnnalsATS. 202004-317CME. PMID: 33202144; PMCID: PMC7919160. (Year: 2021).*

"IEEE Recommended Practice for Application of Controllers and Automation to Industrial and Commercial Power Systems," in IEEE P3001.11/D8, Oct. 2015 , vol. No., pp. 1-81, Jan. 1, 2015. (Year: 2015).*

W. Kastner, G. Neugschwandtner, S. Soucek and H. M. Newman, "Communication systems for building automation and control," in Proceedings of the IEEE, vol. 93, No. 6, pp. 1178-1203, Jun. 2005, doi: 10.1109/JPROC.2005.849726. (Year: 2005).*

* cited by examiner

MEDICAL DEVICE, SYSTEM AND METHOD FOR INTERACTION WITH A SUPPLY FACILITY

This application claims the benefit of German Patent Application No. DE 10 2022 212 368.9, filed on Nov. 18, 2022, which is hereby incorporated by reference in its entirety.

BACKGROUND

Independent of the grammatical term usage, individuals with male, female, or other gender identities are included within the term.

The present embodiments relate to a medical device, a system consisting of a medical device, and a supply facility.

Medical devices may be different imaging or therapeutic apparatuses. For example, the present embodiments relate to medical devices that have a high level of requirement for a resource (e.g., energy or cooling) that cannot be achieved permanently and/or simultaneously for a plurality of these medical devices by the supply facility.

Magnetic resonance tomography systems are imaging apparatuses that, to image an examination object, align nuclear spins of the examination object with a strong external magnetic field and, via an alternating magnetic field, excite the nuclear spins to precession about this alignment. The precession and/or the return of the spin from this excited state into a state with lower energy itself generates an alternating magnetic field as the response, which is received via antennae.

With the aid of magnetic gradient fields, a position encoding is impressed upon the signals, which subsequently enables an allocation of the received signal to a volume element. The received signal is then evaluated, and a three-dimensional imaging representation of the examination object is provided.

For the generation of the magnetic fields and high frequency signals, high power levels in the kilowatt range are required, and a corresponding power output is to be conducted away again by a cooling system.

In X-ray systems such as, for example, computed tomography systems, high electrical power levels are also required to produce the X-rays, as well as cooling of the target in the X-ray sources. The same applies to radiation therapy devices.

Therefore, due to the limited efficiency of the supply facility, it may be that the medical device may only be operated on a temporary basis. For example, in a plurality of medical devices, with simultaneous operation, an overloading of the supply facility that hinders or interrupts operation may occur.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a device and a method that make operation of a medical device more reliable are provided.

For a planned activity, the medical device according to the present embodiments at least temporarily needs a supply of a resource from a supply facility. Medical devices within the meaning of the present embodiments are, for example, imaging apparatuses such as magnetic resonance tomography systems or computed tomography systems, but also therapeutic apparatuses such as, for example, linear accelerators for radiation therapy or combination devices. Accordingly, the activity may be a planned image acquisition or a required irradiation.

Resources needed for the activity may be, for example, a required electrical energy or a cooling agent required to conduct away waste heat. Also conceivable are other resources such as gases, liquids, or other fuels required for the activity.

The medical device has a device control system that controls and coordinates the activities of the magnetic resonance tomography system. For example, planned activities are known to the device control system before the execution in that the planned activities are communicated by way of an operating interface to the device control system for execution. The device control system may be part of the medical device or a spatially distinct device control system that is in signal connection with the medical device.

Further, the medical device and/or the device control system of the medical device has an interface for communication with the supply facility. The interface may be, for example, a serial or a parallel interface, a data net such as Ethernet, or a wireless interface such as WLAN or Bluetooth. In one embodiment, proprietary interfaces (e.g., optical) may be provided in order to prevent disturbances to the imaging.

The device control system is configured to communicate with the supply facility via the interface to the resource, to notify the resource facility of a requirement for a resource or to obtain an approval for using the needed resource or to receive a predetermined quantity of the resource from the supply facility.

In an advantageous manner, the medical device may communicate via the interface with the supply facility in order to provide the availability of the resources needed and to enable undisrupted operation. The medical device may also react in this way to a restricted availability of a resource.

The system according to the present embodiments has a medical device according to the present embodiments and a supply facility. In one embodiment, the supply facility has an interface in order to communicate with the medical device. The supply facility is configured to receive a notification regarding the resource requirement from the medical device according to the present embodiments and/or to send an instruction to the medical device regarding the use of the resource.

Using the notification, the medical device may communicate a resource requirement to the supply facility, so that the supply facility may provide the resource dependent upon the notification, for example, at the requested time point and/or in the requested quantity. Conversely, it is also possible that the medical device may react in this way to a limited availability of a resource.

In one embodiment, a supply control system of the supply facility evaluates the notification and establishes a time point at which the resource may be provided. The supply facility sends an information item to the medical device using an instruction as to when the requested resource is ready and/or an instruction to use the resource.

In an advantageous manner, the system according to the present embodiments consisting of the medical device and the supply facility enables an adjustment and therefore a reliable supply with the resources needed for the planned activity.

The method according to the present embodiments is provided for operating a medical device according to the present embodiments with a supply facility according to the present embodiments.

In one act, a supply control system of the supply facility establishes an availability of a resource needed by the medical device according to the present embodiments.

The availability may relate to a time point at which a needed resource may be provided. If, for example, the resource requirement is below a threshold value, this time point may be at any time. In one embodiment, the supply facility has a buffer for the resource and may provide the resource only upon reaching a fill level of the buffer. An establishment for a plurality of medical devices at a supply facility shared in common with shared resources is set out below.

The availability may, however, also relate to a quantity of the resource that may be provided by the supply facility, either currently or at a time point in the future. For example, the supply facility may establish an electrical power level that is available or a quantity of coolant.

In a further act, the supply control system of the supply facility sends an instruction to the medical device according to the established availability.

For example, the instruction may specify as the availability, a time point and/or a time period for the medical device at which the needed resource will be provided. Therein, the instruction in the form of a control instruction may itself trigger the execution of the activity at this time point. In one embodiment, the device control system of the medical device itself triggers the planned activity at the communicated time point, for example, by the planned activity being entered, according to the time point in the instruction, in an execution table/schedule at this time point for execution and is started at the time point by a so-called scheduler of the medical device.

However, it is also possible that the availability specifies the quantity or quantity per unit time and/or power output that is available to the medical device.

In a further act, according to the instruction received, the planned activity is then carried out by the medical device according to the availability.

If the availability relates to the time point at which the needed resource is ready, it is conceivable, for example, that the medical device starts the planned activity at the specified time point at which the requested resource is available.

However, the availability may specify the quantity and/or power output. The medical device then carries out the planned activity in a modified manner (e.g., by the energy consumption being reduced via an amended sequence and/or an amended mode of execution with a reduced power requirement).

The method according to the present embodiments shares the advantages of the medical device and the system according to the present embodiments.

In one embodiment of the system, the system has a plurality of medical devices. These may also be of different types. The plurality of medical devices are configured to receive an instruction from the supply facility to carry out the planned activity (e.g., dependent upon the instruction; at a time point given in the instruction).

The supply facility itself is configured to receive a plurality of notifications from the plurality of medical devices.

The supply facility is configured, making use of the plurality of notifications, to establish a time plan in which the needed resources may be provided to the plurality of medical devices. More detail in relation to one embodiment is set out in greater detail below.

Further, the supply facility is configured to send instructions to the plurality of medical devices so that the plurality of medical devices may carry out the respective activities (e.g., that the resources needed for the planned activities may be provided by the supply facility). More detail in relation also thereto regarding one embodiment is described in greater detail below.

In one act, the device control system of the medical device establishes a resource requirement for the planned activity. The planned activity may be, for example, an image acquisition that is set via an operating interface at the medical device or remotely. Based on the planned activity, the device control system may establish the requirement for resources for the activity. In a magnetic resonance tomography system, for example, the current requirement of the gradient amplifier, the current requirement for the high frequency excitation, and the current requirement for the cooling may be established for the planned sequence. The information may then be given as a mean value of the power level needed, and a time period may be given as information in the notification. In one embodiment, a maximum value is provided rather than the mean value or an exact temporal current pattern over the time period of the activity. In the same way, a requirement for coolant as a resource may be predicted based on the heating caused by the energy supply and may be communicated as information.

Similarly, for other modalities such as CT or X-ray devices or devices for radiation therapy, an energy requirement and/or coolant requirement may be established and provided as information.

In one embodiment, the prediction of the requirement for other operating supplies, such as technical gases or a contrast medium, may be provided.

In a further act, the device control system sends the established information via the interface as a notification to the supply facility, so that the supply facility is informed about the resource requirement and/or the time point and/or the time period of the resource requirement.

A possible embodiment of the method relates to a system consisting of a supply facility and a plurality of medical devices. The respective medical devices establish, as previously described, a resource requirement for each planned activity. The respective activities of the medical devices may be different and, for example, planned for any desired time points (e.g., independently of one another and independently of an availability of the resources). Planned activity may be that a time point of a start and/or a time period of an execution is provided, although the activity does not necessarily take place exactly at this time point. For example, the planned activity may relate to medical devices in different organizational units such as departments of a hospital. Only the shared supply facility is in common, the resources of which are to be shared by the plurality of medical devices.

The plurality of the medical devices establishes in one act, as described above, a resource requirement for the planned activity, each independently for itself (e.g., without taking account of each of the other medical devices).

In a further act, the plurality of medical devices send a notification to the supply facility according to the established resource requirement. In one embodiment, the notification contains a quantitative specification regarding the resource needed. For example, an average or a required peak power level for electrical energy may be specified. A specification of the electrical energy required altogether may also be provided. In one embodiment, a time specification is also contained in the notification (e.g., relating to a planned start of the planned activity and therewith the extraction of the resource; possibly also relating to the duration and/or the time period of the extraction). In one embodiment, an information item relating to a detailed temporal sequence with time point and requirement may be provided.

In one embodiment, no time point is specified in the notification; therefore, an immediate extraction requirement is signaled, or an extraction is signaled as soon as possible after approval by the supply facility in a subsequent step.

As described above, the resource in question may be, apart from electrical energy, coolant and/or cooling capacity or another operating supply such as technical gases.

In a further act, the supply control system of the supply facility establishes a time point at which the needed resource may be provided to the respective medical device. For this purpose, different scenarios may be provided. What the different scenarios have in common is that the supply control system establishes the time points such that the sum of the resources needed simultaneously by the plurality of medical devices never exceeds the resources available to the supply facility.

For example, the supply control system may sum the respective resources required and/or requested at one time point. Provided this sum remains below a limit of the required resources that may be provided by the supply facility, the supply control system may approve the resources accordingly in an instruction to the medical device. For example, the limit may be an electrical power level that may be provided by the supply facility or a maximum coolant flow rate.

If the required and/or requested resources exceed the available resources and/or the limit, the supply control system may transfer an information item to the medical device in an instruction as to when the requested resource is available to the medical device, or sends the instruction to the medical device at this time point and thereby releases the resource.

The supply control system may establish, for example, when resources are available again by one of the preceding requests having ended. In one embodiment, the notifications regarding the required resources have an identification of the medical device, and the supply control system undertakes a prioritization dependent upon the identification or the notification itself has an information item regarding the priority of the request. Resources becoming free may then be released by the supply control system following the prioritization of the medical device (e.g., medical devices with high priority receive the resource sooner).

In a further act, the medical device then carries out the activity in accordance with the instruction from the supply control system. This may be, for example, that the medical device carries out the activity on receiving the instruction. In one embodiment, the instruction has an information item relating to a time point or time period of the execution. Then, the medical device and/or the device control system may start the activity at the time point predetermined by the instruction. In one embodiment, execution is confirmed by a user at the medical device. For example, the device control system on the medical device may create an output for an operating person who confirms the output via an input at an operating element. In one embodiment, a selection of different time points or a possible time period for the operating person may be output.

The above-described properties, features, and advantages of the present embodiments and the manner in which the above-described properties, features, and advantages are achieved are made more clearly and distinctly intelligible with the following description of the embodiments that are set out in greater detail making reference to the drawings.

DETAILED DESCRIPTION

Figure 1:
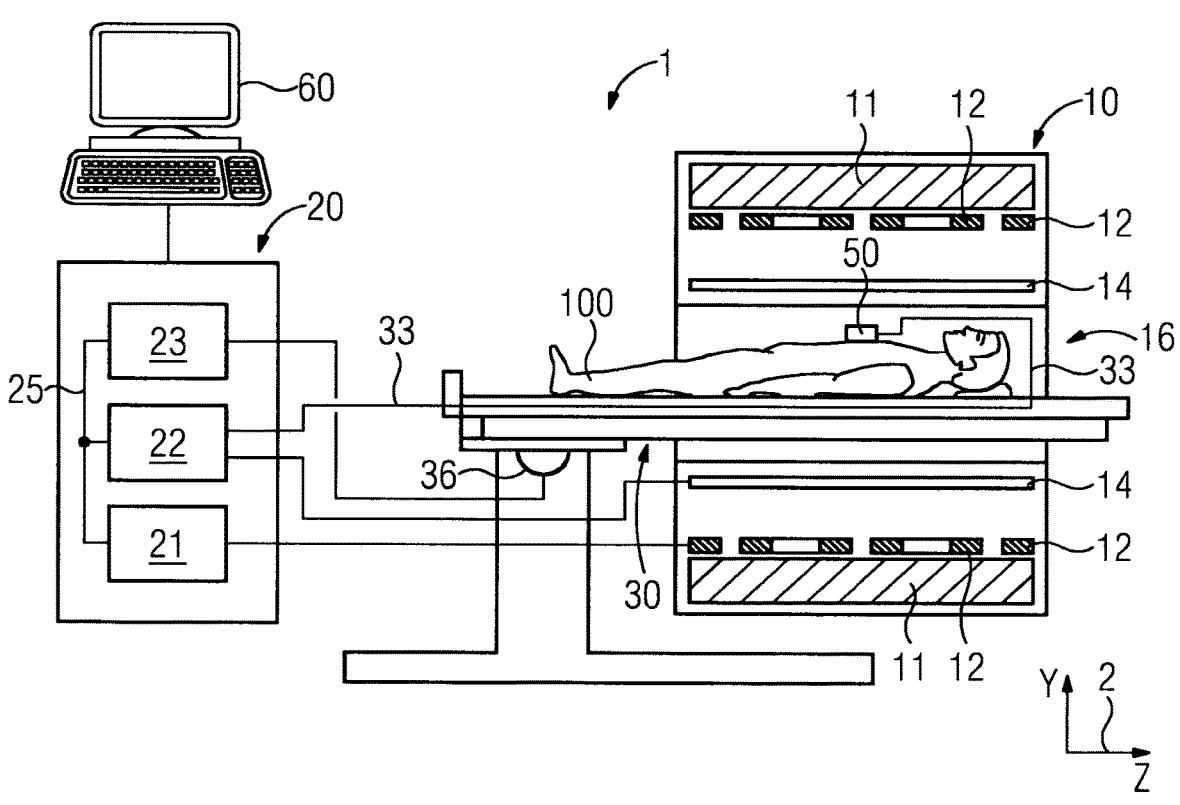
FIG. 1 shows a schematic representation of an example of a medical device according to the present embodiments.

FIG. 1 shows a schematic representation of an embodiment of a magnetic resonance tomography system 1 as an example of a medical device.

A magnet unit 10 has a field magnet 11 that generates a static magnetic field BO for aligning nuclear spins of samples and/or of a patient 100 in a scanning region. The scanning region is characterized by an extremely homogenous static magnetic field BO, where the homogeneity relates, for example, to a magnetic field strength and/or a magnitude. The scanning region is almost spherical and is arranged in a patient tunnel 16 that extends in a longitudinal direction 2 through the magnet unit 10. A patient support 30 is movable in a patient tunnel 16 by a displacement unit 36. Typically, the field magnet 11 is a superconducting magnet that may provide magnetic fields with a magnetic flux density of up to 3 T and, in the newest devices, even higher. For weaker field strengths, however, permanent magnets or electromagnets with normally-conducting coils may also be used.

In order to maintain the low temperatures, the superconducting magnet needs a cooling assembly with a high current consumption and simultaneously high waste heat levels and consequent cooling requirement.

The magnet unit 10 further includes gradient coils 12 that are configured, for spatial differentiation of the acquired imaging regions in the examination volume, to overlay temporally and spatially variable magnetic fields onto the BO magnetic field in three spatial directions. The gradient coils 12 may be coils made of normally-conducting wires that may generate mutually orthogonal fields in the examination volume.

The resistive gradient coils 12 are also driven by a gradient control system 21 with very high currents and have a corresponding requirement for electric energy and cooling for the waste heat.

The magnet unit 10 also has a body coil 14 that is configured to emit a high frequency signal fed via a signal line into the examination volume, receive resonance signals emitted from the patient 100, and pass the resonance signals on via a signal line.

A control unit 20 supplies the magnet unit 10 with the different signals for the gradient coils 12 and the body coil 14 and evaluates the received signals.

Thus, the control unit 20 has the gradient controller 21 that is configured to supply the gradient coils 12 via feed lines with variable currents that provide the desired gradient fields in the examination volume in a temporally coordinated manner.

Further, the control unit 20 has a high frequency unit 22 that is configured to generate a high frequency pulse with a pre-determined temporal sequence, amplitude, and spectral power distribution for the excitation of a magnetic resonance of the nuclear spins in the patient 100. Thereby, pulse power levels in kilowatt range may be achieved. The excitation signals may be emitted via the body coil 14 or via a local transmitter antenna into the patient 100.

A device control system 23 communicates via a signal bus 25 with the gradient controller 21 and the high frequency unit 22.

In order to receive the magnetic resonance signal, a local coil 50 according to the present embodiments is arranged on the patient 100 in the patient tunnel 16 in order to acquire magnetic resonance signals from an examination region in the direct vicinity with the greatest possible signal-to-noise ratio. The local coil 50 is in signal connection via a connecting line 33 to a receiver in the high frequency unit 22.

Further, the magnetic resonance tomography system 1 has an interface, for example, to a data network 300, via which the device control system 23 may communicate with a supply control system 320 of a supply facility 310 (e.g., to send notifications and to receive instructions).

Figure 2:
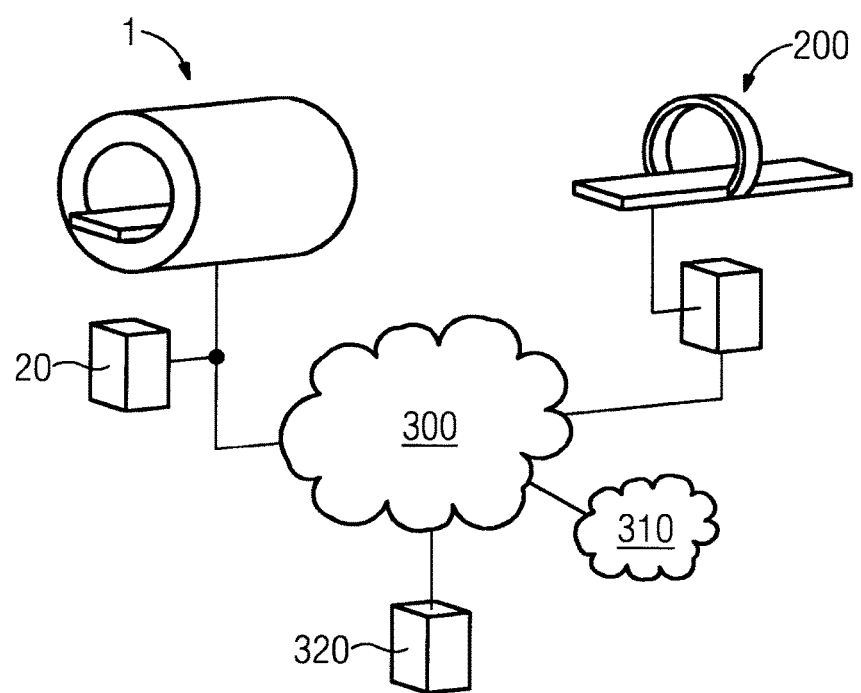
FIG. 2 shows a schematic representation of an example of a system according to the present embodiments.

FIG. 2 shows an example of a system according to the present embodiments.

The magnetic resonance tomography system 1 and/or a device control system 20 of the magnetic resonance tomography system 1 is connected to the data network 300. The data network 300 may be, for example, a LAN or a WAN such as an IP network. WAN networks such as mobile radio networks may also be provided.

Further, as an example of a further modality, a computed tomography system 200 is connected to the data network 300. The computed tomography system 200 also has a significant energy requirement for generating X-ray beams and a corresponding cooling requirement for conducting away the heat generated. The computed tomography system 200 is also in signal-carrying connection, by its device control system 23 via the data network 300, with the supply control system 320 in order to exchange notifications and instructions in accordance with the method according to the present embodiments.

Further, as medical devices, other devices with a significant requirement for electrical energy, cooling, or other operating supplies may be provided, such as, for example, linear accelerators for radiation therapy.

The supply facility 310 may be, for example, a central in-house services system from which the current supply, water, and air conditioning are provided. In one embodiment, however, a public "smart" and/or intelligent current supply is provided, where, via an interface, the requirement may be announced and allocated and/or provided according to the resource situation. The resource provided by the supply facility 310 may, however, also relate to technical gases or suchlike. The supply control system 320 may therein be an integral component of the supply facility 310. In one embodiment, however, an offset and/or centralized supply control system 320 is provided.

Figure 3:
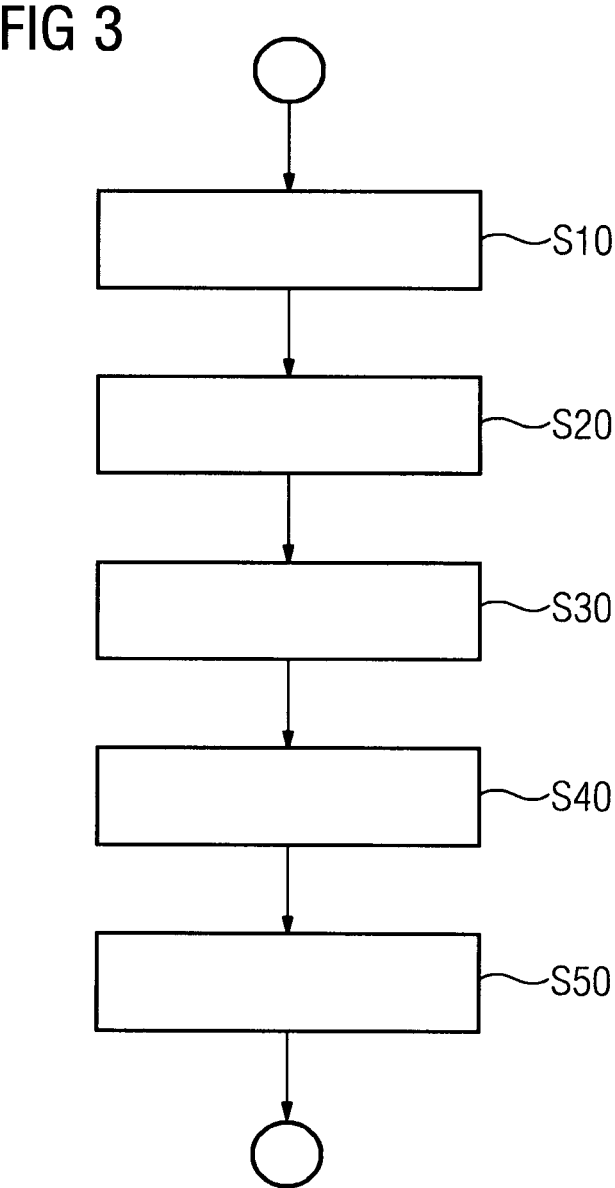
FIG. 3 shows a schematic flow diagram of a method according to the present embodiments.

FIG. 3 shows a schematic flow diagram of an embodiment of a method according to the present embodiments.

The method according to the present embodiments relates to a system of one or more medical devices and a supply facility 310 as shown, by way of example, in FIG. 2.

In act S10, a device control system 23 of a medical device establishes a resource requirement for a planned activity.

For a magnetic resonance tomography system 1 as the medical device, for example, energy for a cooling unit of the superconducting field magnet 11 to maintain the low temperatures needed for the superconduction is provided. The cooling of the field magnet 11 is almost independent of the image acquisition and may represent a substantially constant energy requirement in the range of one to several kilowatts. In one embodiment, the energy requirement for the cooling unit is intermittent in the sense that, due to the heat capacity of the magnet, times with an active cooling unit are interrupted by pauses without operation. The energy requirement for the cooling may therein be acquired as a mean value, as a peak value, or in a mixed calculation. This, for example, depends upon the supply facility 310, according to whether it is restricted primarily by a maximum peak power level that is capable of being delivered or by a buffer store to a maximum mean load. In one embodiment, the medical device itself has buffer stores for the resource in order to limit and/or reduce the peak requirement to the external supply facility.

A further substantial factor is the energy requirement for generating the gradient fields. In order to generate these, the gradient control system 21 feeds the usually resistive gradient coils 12 with currents up to several 100 amps or even kiloampere. The energy requirement is therein time-dependent and limited to the time of the sequence in which the gradient fields are needed. The power needed may therein also vary during the generation of a gradient (e.g., in order to compensate for effects due to the inductance of the gradient coils by the voltage being adapted). As set out above with regard to the energy requirement of the cooling of the field magnet 11, the energy requirement may be established as a peak value by adding the (e.g., simultaneously occurring) maximum values and/or mean values.

A further substantial energy consumer is the high frequency unit 22 that, in order to excite the nuclear spin, generates a high frequency pulse and radiates the high frequency pulse, for example, using the body coil 14. Here also, high frequency power levels in the kilowatt range are needed, which, however, are needed essentially only briefly during the excitation pulse.

In one embodiment, the energy requirement may be established as a peak value by adding the (e.g., simultaneously occurring) maximum values and/or mean values. For example, an excitation may take place simultaneously at least under simultaneous application of a gradient field for the selection of a slice.

A further needed resource for the operation of the magnetic resonance tomography system 1 is a cooling in the form of a cooling power level of a cooling unit and/or the availability of a cooling fluid for conducting away the heat generated. The electrical power levels of the gradient control system 21 and the high frequency unit 22 contribute to the fields generated to only a very small extent but are largely converted into waste heat. In the cooling of the field magnet 11, there also arises the heat absorbed from the environment. The cooling power level needed and/or the heat loss to be conducted away may be established via the electrical energy utilized, as previously determined. In one embodiment, it is possible to weight this further in the calculation with an efficiency factor of greater than 1 for the cooling of the field magnet, since herein the cooling unit operates comparably to a heat pump. Due to the heat capacities of gradient coils, the cooling unit, the power amplifiers, and their cooling bodies, herein, a value temporally averaged over a predetermined timespan may be used, equivalent to a low-pass filter.

Similarly, the resource requirement for other medical devices such as an X-ray device and/or a computed tomography system 200 may be established. In an X-ray device, a substantial energy consumer is the X-ray source. First, an electron beam that may require power levels in the kilowatt range is needed (e.g., due to the high voltage in the kilovolt range, despite the relatively small currents). In most X-ray sources, the X-ray radiation is generated as braking radiation, where most of the electrical energy expended is again converted into heat that is then to be conducted away with a cooling medium.

A similar principle applies to devices for radiation therapy as the medical device. Herein also, a particle beam is to be accelerated with a high voltage. If the particle beam itself is not used for irradiation, the particle beam is converted by a target into high-energy photons, as in an X-ray tube. The heat loss is again to be conducted away from the target. Further, in a device for radiation therapy, electromagnets may be provided to deflect the beams that themselves require significant currents and also generate heat accordingly. In order to determine the electrical energy and cooling needed, the relationships described above in relation to the magnetic resonance tomography system may be used. In one embodiment, however, the resources needed are distributed more evenly over the time of the activity, and therefore, a mean value may be adequate.

In a further act S20, the device control system 23 sends a notification with information relating to the established resource requirement to the supply control system 320. The information may be, for example, an established mean resource requirement or a peak and/or maximum value. In one embodiment, an information item regarding the time point of the requirement is part of the notification. In one embodiment, the information item includes a start and/or an end and/or a start and a duration of the resource requirement. In one embodiment, the information item includes an exact temporal sequence of the requirement, comparable with a graph over time in which the time is shown on the abscissa and the respective requirement on the ordinate. In one embodiment, the information item includes no stipulation of time, where, for example, this may be, depending upon the embodiment, that the resource is needed immediately or as soon as possible (e.g., upon an approval by the supply control system in an instruction as described below).

In a further act S30, the supply control system 320 establishes an availability of the resource. This may be, first, a time point at which the needed resource and/or resources may be provided to the originally needed extent.

On a single request for the resource, the supply control system compares, for example, whether the resource requested by the first medical device is less than or equal to the remaining resource. It is, for example, also conceivable that another second medical device already needs a portion of the resource and that its activity cannot be interrupted. If the remaining available residue of the resource is then greater than the requirement for the resource communicated in the notification, then the resource is available immediately.

If the remaining residue is less than the requested requirement for the resource, the time point may be, for example, when the second medical device has ended its activity.

The availability may, however, also be the quantity currently available or available at a particular time point or a quantity per time period and/or a power level of a resource.

In one embodiment, a plurality of medical devices have signaled a requirement with a notification to the supply control system 320 (e.g., with a temporal sequence). The supply control system 320 may then establish, by different temporal displacements of the activities, a temporal constellation and/or time plan of the activities with which at no time point do the total of the resources needed exceed a maximum peak value and/or a mean value. It is therein conceivable that the supply control system 320 undertakes a prioritization of the medical devices (e.g., allocates the resource, in each case, to the medical device with the highest priority, so that this device may carry out the activity at the earliest possible time point).

If different resources are needed and requested for an activity, the supply control system accordingly establishes the time point such that at no time point does the total of all the needed resources exceed a maximum peak value and/or a mean value per resource.

It is therein conceivable that the supply control system 320 reserves the resources according to the established time plan so that the resources are then available at the established time point. In this case, subsequently arriving notifications with requests for resources are to be put back, and/or time points and/or a time plan that puts back the later requests is to be established. Also possible would be a conversion of the time plan before the execution of an activity if the later request has a higher priority.

In one embodiment, the supply control system 300 distributes the available resources to the requesting medical devices according to a predetermined key (e.g., following a prioritization of the devices or their capability for reducing the resource requirement of an activity).

In a further act S40, the supply control system 320 sends an instruction to the medical device according to the established availability. The instruction may specify, for example, a time point at which the medical device may start the activity. In one embodiment, in the simplest case, an instruction to carry out the activity, in response to which the medical device may carry out said activity immediately, is provided.

The instruction may also specify an available quantity of the resource. If the available resource is less than the resource requested for the planned activity, the medical device may adapt the planned activity to the available resource. In one embodiment, for example, in the case of a magnetic resonance tomography system, a sequence with a lower absolute or peak resource requirement is selected. In one embodiment, by way of a temporal extension of the activity, a peak demand is reduced.

Also possible are more complex sequences, in which the medical device confirms the instruction with a confirmation or declines the instruction with a refusal. The confirmation may specify, for example, that the medical device is carrying out the activity at the time point, for example, immediately or at the time point in the future. A refusal may be, for example, that the time point is too late and/or the activity and thus the resource is no longer needed.

In one embodiment, in the refusal, an information item relating to a prioritization is given, so that the supply control system 320 repeats the act S30 with this prioritization and establishes a new time point.

In a further act, the medical device carries out the planned activity according to the received instruction. For example, the magnetic resonance tomography system 1 begins a sequence for image acquisition, or the computed tomography system 200 starts the recording at the time given in the instruction.

In one embodiment, it is part of the execution that a message regarding the impending activity is issued via an operating interface 60 to a person operating the medical device, and only upon confirmation by the operating person via the operating interface 60 is the execution started.

Although the invention has been illustrated and described in detail via the embodiments, the invention is not restricted by the examples disclosed, and other variations may be derived herefrom by a person skilled in the art without departing from the protective scope of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A medical device that, for a planned activity, at least temporarily needs one or more resources from a supply facility, the medical device comprising:
   a device control system configured to establish, for the planned activity, a resource requirement for the one or more resources; and
   an interface configured for communication with the supply facility regarding the one or more resources, the communication with the supply facility comprising information relating to the established resource requirement,
   wherein the one or more resources include cooling for the medical device, and
   wherein the device control system is configured to communicate with the supply facility via the interface, such that the supply facility is notified of the established resource requirement for the one or more resources.

2. The medical device of claim 1, wherein the device control system is configured to:
   establish a resource requirement for the planned activity; and
   by a notification, communicate via the interface with the supply facility.

3. The medical device of claim 1, wherein the device control system is configured to:
   receive an instruction for using the one or more resources from the supply facility via the interface; and
   carry out the planned activity dependent upon the instruction.

4. The medical device of claim 1, wherein the one or more resources further include energy.

5. The medical device of claim 1, wherein the medical device is a device for radiation therapy, an imaging modality, or a combination thereof.

6. The medical device of claim 5, wherein the medical device is the imaging modality or the combination thereof, and
   wherein the imaging modality is a magnetic resonance tomography system or a computed tomography system.

7. The medical device of claim 1, wherein the cooling is in the form of a cooling power level of a cooling unit of the medical device, availability of a cooling fluid for the medical device, or a combination thereof.

8. The medical device of claim 1, wherein the device control system is further configured to receive a predetermined quantity of the one or more resources from the supply facility.

9. A system comprising:
   a medical device that, for a planned activity, at least temporarily needs one or more resources from a supply facility, the medical device comprising:
      a device control system; and
      an interface configured for communication with the supply facility regarding the one or more resources, wherein the device control system is configured to establish a resource requirement for the planned activity, and by a notification, communicate the established resource requirement for the planned activity, via the interface, to the supply facility; and
   the supply facility, which includes a supply control system, the supply control system being configured to:
      receive the notification regarding the resource requirement; and
      dependent upon the notification, provide the needed one or more resources, wherein the one or more resources include cooling.

10. The system of claim 9, wherein the device control system is further configured to:
    receive an instruction for using the one or more resources from the supply facility via the interface; and
    carry out the planned activity dependent upon the instruction, and
    wherein the supply control system is further configured to:
       receive the notification regarding the resource requirement from the medical device;
       establish a time point at which the needed one or more resources are providable; and
       in the instruction, send an information item regarding the time point to the medical device.

11. The system of claim 10, further comprising a plurality of medical devices, the plurality of medical devices comprising the medical device,
    wherein the device control system is configured to:
       receive an instruction for using the one or more resources from the supply facility via the interface; and
       carry out the planned activity dependent upon the instruction,
    wherein the supply control system is further configured to:
       receive a plurality of notifications from the plurality of medical devices;
       establish a time plan according to which the needed one or more resources are providable to the plurality of medical devices; and
       send instructions to the plurality of medical devices, so that medical devices of the plurality of medical devices are operable to carry out the respective activity according to the time plan.

12. A method for operating a system, the system comprising a medical device that, for a planned activity, at least temporarily needs one or more resources from a supply facility, the medical device comprising a device control system and an interface configured for communication with the supply facility regarding the one or more resources, wherein the device control system is configured to establish a resource requirement for the planned activity, and by a notification, communicate the established resource requirement for the planned activity, via the interface to the supply facility, the system further comprising the supply facility, which includes a supply control system, the supply control system being configured to receive the notification regarding the resource requirement and dependent upon the notification, provide the needed one or more resources, the method comprising:

establishing an availability of a needed resource via the supply control system;

sending an instruction from the supply control system to the medical device according to the established availability; and carrying out the planned activity via the medical device according to the received instruction, wherein the one or more resources include cooling.

13. The method of claim 12, further comprising:

establishing a resource requirement for the planned activity via the device control system of the medical device; and sending an information item regarding the established resource requirement in a notification via the medical device to the supply facility.

14. The method of claim 13, wherein the system comprises a plurality of medical devices, the plurality of medical devices comprising the medical device, and wherein the method further comprises:

establishing, by the plurality of medical devices, in each case, a resource requirement;

sending a notification to the supply control system; and establishing, by the supply control system, a time point at which the needed resource is providable to the respective medical device.

* * * * *